United States Patent
Orlowski et al.

(10) Patent No.: US 6,696,043 B2
(45) Date of Patent: Feb. 24, 2004

(54) TEETH WHITENING COMPOSITION IN THE FORM OF A CHEWING GUM

(75) Inventors: Jan A. Orlowski, Altadena, CA (US); David V. Butler, West Covina, CA (US); Amy P. Noss, Cleveland Heights, OH (US); Mahin Mapar, San Dimas, CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 0 days.

(21) Appl. No.: 09/931,634

(22) Filed: Aug. 16, 2001

(65) Prior Publication Data

US 2002/0076384 A1 Jun. 20, 2002

Related U.S. Application Data

(60) Provisional application No. 60/234,033, filed on Sep. 20, 2000.

(51) Int. Cl.[7] .............................. A61K 9/68; A61K 9/20
(52) U.S. Cl. ........................ 424/48; 424/440; 424/53; 426/3; 426/4; 426/5
(58) Field of Search ...................... 424/48–58; 426/3–5

(56) References Cited

U.S. PATENT DOCUMENTS

| | | | | | |
|---|---|---|---|---|---|
| 3,886,265 A | * | 5/1975 | Evers et al. | .................. | 424/49 |
| 4,302,441 A | * | 11/1981 | Muhlemann et al. | ......... | 424/48 |
| 4,400,372 A | * | 8/1983 | Muhler | ........................ | 424/48 |
| 4,568,537 A | * | 2/1986 | Hoerman | .................... | 424/48 |
| 4,906,455 A | * | 3/1990 | Hoerman | .................... | 424/48 |
| 4,925,655 A | * | 5/1990 | Smigel et al. | ................. | 424/52 |
| 5,057,328 A | * | 10/1991 | Cherukuri et al. | | |
| 5,106,632 A | * | 4/1992 | Wong et al. | .................... | 426/3 |
| 5,116,602 A | * | 5/1992 | Robinson et al. | ............. | 424/49 |
| 5,487,902 A | * | 1/1996 | Andersen et al. | ............... | 426/3 |
| 5,496,558 A | * | 3/1996 | Napolitano et al. | ......... | 424/435 |
| 5,500,207 A | * | 3/1996 | Goulet | ......................... | 424/54 |
| 5,585,110 A | * | 12/1996 | Kalili et al. | ................. | 424/440 |
| 5,693,334 A | * | 12/1997 | Miskewitz | ................... | 424/440 |
| 5,698,215 A | * | 12/1997 | Kalili et al. | ................. | 424/440 |
| 5,908,614 A | * | 6/1999 | Montgomery | ................. | 424/48 |
| 5,972,374 A | * | 10/1999 | Theisen | ...................... | 424/440 |
| 6,221,340 B1 | * | 4/2001 | Yu et al. | ........................ | 424/49 |
| 6,221,341 B1 | * | 4/2001 | Montgomery | ................. | 424/53 |
| 6,235,318 B1 | * | 5/2001 | Lombardy et al. | .............. | 426/3 |
| 6,290,934 B1 | * | 9/2001 | Kramer et al. | ................. | 424/53 |
| 6,312,670 B1 | * | 11/2001 | Montgomery | ................. | 424/53 |
| 6,322,773 B1 | * | 11/2001 | Montgomery | ................. | 424/53 |
| 6,365,134 B1 | * | 4/2002 | Orlowski et al. | .............. | 424/53 |
| 6,447,757 B1 | * | 9/2002 | Orlowski et al. | .............. | 424/53 |

FOREIGN PATENT DOCUMENTS

| | | | |
|---|---|---|---|
| EP | 269571 | * | 2/1989 |
| EP | 446170 | * | 9/1991 |
| FR | 2079005 | * | 12/1971 |

* cited by examiner

*Primary Examiner*—Shep K. Rose
(74) *Attorney, Agent, or Firm*—Knobbe, Martens, Olson & Bear, LLP

(57) ABSTRACT

Described herein is a novel teeth whitening chewing gum formulation comprising bivalent metal peroxide(s) and anhydrous organic acids. Upon mastication in the oral environment, the acids react with the peroxide to form hydrogen peroxide in situ, in an environment stimulating the decomposition of such peroxide to form water and radical oxygen. The system is characterized by its efficacy and convenience. The teeth whitening composition of the preferred embodiment is also virtually insensitive to storage conditions, allowing for an extended shelf life.

46 Claims, No Drawings

TEETH WHITENING COMPOSITION IN THE FORM OF A CHEWING GUM

RELATED APPLICATIONS

This application claims priority under 35 U.S.C. §119 of provisional application Ser. No. 60/234,033, filed Sep. 20, 2000.

FIELD OF THE INVENTION

This invention relates to the field of tooth whitening using chewing gum.

BACKGROUND OF THE INVENTION

Teeth whiteners, also known as teeth bleaching agents, are in widespread use as a cosmetic means to enhance appearance and to contribute to better oral health and hygiene in general.

Among teeth whitening formulations, those containing oxidizing agents as active ingredients are preferred because of their fast action and superior efficacy. The most frequently employed peroxide in teeth whitening materials is hydrogen peroxide, either in free form or as an adduct with urea known as carbamide peroxide.

Prior art devices can be classified in three groups based on the method of delivering the material to tooth surfaces. The first is whitening toothpastes, in which bleaching agents are typically incorporated as an additional feature in toothpaste formulations. Another category contains formulations intended specifically for whitening teeth, usually in gel form, which are typically delivered to the tooth surface by fabricated trays. Such materials may be administered under the control of a dental professional or designed for in-home use. Finally, the newest trend in tooth whitening devices involves chewing gum products.

Chewing gum whitening products offer an attractive alternative to more cumbersome and time intensive whitening systems because they are substantially more user friendly. People find chewing gum pleasurable, and are willing to chew gum for much longer periods of time than they typically wear trays or brush their teeth. Such a method of delivery offers whitening action without sacrifice of time or comfort.

The common shortcoming of most prior art peroxide-based teeth whitening devices, especially those based on hydrogen or carbamide peroxides, is their instability. The efficacy of such materials deteriorates over time, particularly when exposed to elevated temperatures. Chewing gums of the prior art are more vulnerable than other whitening devices to the loss of efficacy upon storage because they require the use of anhydrous peroxides. This makes carbamide peroxide the active ingredient of choice, because it is the most effective of the peroxides of traditional bleaching formulations available in a dry form.

However, carbamide peroxide is particularly prone to accelerated decomposition when in contact with common ingredients of chewing gums (e.g. particulate matter such as calcium bicarbonate, or other alkaline materials). The use of stabilizing additives is therefore counterproductive because incorporation of such materials negatively affects the product's whitening efficacy. Stability is therefore in direct conflict with the purpose and objective of their applications, namely achieving the best possible whitening effect in a reasonable length of contact with the tooth surface. Since the efficacy of the material is of greater concern, the shelf life of most prior art chewing gum teeth whitening formulations is extremely limited.

Thus, the shortcomings of prior art teeth whitening chewing gum formulations may be summarized as follows:

A) The inherent conflict between the requirements of shelf life stability of peroxides and the understandable demand for fast bleaching action and high efficacy of the product. Formulations which exhibit adequate shelf life, as evidenced by maintaining stable peroxide concentrations over time, are intrinsically less effective due to the slow generation of radical (atomic) oxygen in the oral environment which impairs the speed and efficacy of the teeth bleaching process;

B) The difficulty in formulating chewing gums of adequate shelf life due to the vulnerability of anhydrous peroxides, particularly carbamide peroxide, in the presence of common ingredients of chewing gum formulations.

C) Technical difficulties associated with manufacturing of teeth whitening chewing gums in the form of two parts mixed in the mouth during mastication.

SUMMARY OF THE INVENTION

In view of the shortcomings of the prior art, preferred embodiments of the present invention provide a fast acting tooth whitening chewing gum which is virtually insensitive to storage conditions, provides a safe, effective and convenient method for whitening teeth and/or contributes to improved oral health and hygiene. The chewing gum comprises peroxides of the first or second group of the Periodic Table, preferably calcium, zinc and/or strontium, at concentrations corresponding to 1–20% by weight hydrogen peroxide, and anhydrous organic acids, preferably tartaric, citric, lactic, oxalic or mixtures thereof. In one embodiment, the one or more organic acids are at a concentration of 1% to 20% by weight, preferably 8% to 12%. In a further embodiment, the one or more peroxides are at a concentration of 3% to 12% by weight hydrogen peroxide. In one embodiment, the peroxides are calcium peroxide, zinc peroxide, or strontium peroxide. In a further aspect, the pH of a water extract from the chewing gum is between 4 and 11. In a further embodiment, the chewing gum has further hydrophilic additives such as glycerin, propylene glycol, and polyglycols. In a further embodiment, the chewing gum has sweeteners such as xylitol, fructose, sorbitol, sucrose, saccharine, and aspartame. The chewing gum may also contain food grade colorants, flavors, fragrances, and mixtures thereof. Preferably the colorants are FD&C Blue #1 or #2. Preferably the colorants are orange, lemon, peppermint, spearmint, mint, bubble gum, cherry, watermelon, strawberry or apple varieties. The chewing gum may also have fluoride salts, such as sodium fluoride, stannous fluoride, sodium monofluorophosphate, and mixtures thereof.

DETAILED DESCRIPTION OF THE PREFERRED EMBODIMENT

Disclosed herein is a new teeth whitening device delivered to the teeth in the form of a chewing gum. The chemical composition of the device comprises peroxides, preferably of the first or second group of the Periodic Table, preferably calcium, zinc and/or strontium, at concentrations corresponding to 1–20% by weight hydrogen peroxide; and anhydrous organic acids, preferably tartaric, citric, lactic, oxalic or mixtures thereof.

Such constituents of the preferred embodiments are blended with chewing gum base and, optionally, with other desirable ingredients to enhance the texture, consistency, or sensory characteristics of the product.

The formulation of the preferred embodiments differs significantly from prior art teeth bleaching chewing gums in that the active peroxide ($H_2O_2$) is generated in the mouth upon contact of the chewing gum with saliva (which hydrates the anhydrous acids in the gum), as a result of the reaction:

$$MO_2 + 2\ R\text{---}COOH_{(aq)} \rightarrow M(RCOO)_2 + H_2O_2$$

where M is a metal and R is an organic group.

The hydrogen peroxide, which is much less stable than metal peroxides, next undergoes accelerated decomposition in the presence of chemical components of the device or reaction products resulting from such components coming into contact with saliva which act as catalysts in the reaction below:

$$H_2O_2 \xrightarrow{\text{catalyst}} H_2O + O^{\bullet}$$

The rate of generation of radical oxygen (O*) is directly linked to the speed of the teeth whitening process. Oral mastication accelerates the penetration of moisture into the chewing gum, and thus the rate of radical oxygen generation and teeth whitening action.

The peroxides are preferably peroxides of the first or second group of the Periodic Table, preferably calcium or strontium, although other metals such as zinc can be used. It is to be understood that the second group is used herein to refer to elements of Group 2a and 2b of the periodic table of the elements. The peroxides may be mixed and include more than one peroxide whose concentrations when added are between 1 and 20% by weight hydrogen peroxide, including 3% to 7% and about 3% to 12%. The peroxides are preferably at concentrations corresponding to 1–20% by weight hydrogen peroxide. Preferably calcium peroxide is used at concentrations corresponding to 3 to 7% calcium peroxide, including 3.5%, 4%, 4.5%, 5%, 5.5%, 6%, and 6.5%. In other embodiments, the calcium peroxide is used at 3.4 to 4.6% calcium peroxide. The peroxides may also be mixed and include 2, 3, 4, or more different peroxides in any ratio. In one embodiment a mixture of calcium peroxide and zinc peroxide is used and the zinc peroxide is at a concentration of about 0.3 to 0.7% by weight.

The one or more anhydrous organic acids are preferably tartaric, citric, lactic, oxalic or mixtures thereof. The anhydrous organic acids are preferably at about 1% to about 20% by weight, including 1 to 11% by weight, including 2%, 3%, 4%, 5%, 6%, 7%, 8%, and 9%. More preferably the anhydrous organic acids are from 8% to 11% by weight, including 8.5%, 9%, 9.5%, 10%, and 10.5%. The percentage by weight may be a combination of the two or more anhydrous organic acids. If it is found that the acid dissolves in the saliva faster than desired, one may coat the acid or particles of acid with an inert material such as, but not limited to, saccharine, xylitol, polyvinyl acetate and glycerol monostearate.

Chewing gum bases are typically natural products, usually extracts from certain trees, plants, and microbes. They are usually divided into three categories: soft, medium, and hard. The soft and medium varieties are preferred for use in the chewing gum formulations herein. The chewing gum bases commonly used in conventional chewing gum are suitable as ingredients of the formulations of the preferred embodiment. In one embodiment, the chewing gum base is added at between 50 and 90%, including 55%, 60%, 65%, 70%, 80%, and 85% by weight. In a further embodiment, the chewing gum base is added at between 65% and 85%. In a further embodiment, the chewing gum base is added at between 70% and 80%. It is to be understood that substantial quantities of chewing gum additives are used, the concentration may vary.

Optional but desirable additives to the formulation of the preferred embodiments which may have beneficial effects on the rate of decomposition of hydrogen peroxide during the mastication process include, but are not limited to, hydroxides, oxides, and salts of alkaline earth metals, particularly carbonates; hydroxides and carbonates of sodium, calcium and potassium; silicas; and calcium silicate. In one embodiment, the calcium carbonate is added at between 0.5% and 6% by weight, including 1.5%, 2%, 2.5%, 3.5%, 4%, 4.5%, and 5%. In a further embodiment, the calcium carbonate is added at between 1% and 3% by weight.

Hydrophilic additives may be added to the chewing gum base. Examples of hydrophilic additives which may be used includes glycerin, propylene glycol, and polyglycols.

Flavoring and coloring agents may be added to enhance the acceptance or appeal of either or both parts, or as indicators of the reactivity of peroxide and the progress of radical oxygen generation. The most desirable flavors may include, among others, food grade orange, lemon, peppermint, spearmint, mint, bubble gum, cherry, watermelon, strawberry and apple varieties. As coloring agents FD&C or FD&C water soluble dyes may be used; FD&C Blue #1 and FD&C Blue #2 are preferred. In one embodiment, the flavor additive is peppermint oil and it is added at between 0.05 and 0.5%, including 0.075%, 0.15%, 0.2%, 0.3%, 0.4%, and 0.45%. In a further embodiment, the peppermint oil or other flavor additive is added at between 0.1 and 0.4%. Although it is to be understood that the strengths of flavoring differ considerably a much lower or higher concentration may be needed.

Sweeteners may be added to the chewing gum including sucrose, saccharine, aspartame, fructose, xylitol, sorbitol and mixtures thereof. Preferably, the sweetener is xylitol or fructose. In one embodiment, the xylitol, fructose or other sweetener is added at between 1 and 10%, including 2%, 3%, 4%, 5%, 6%, 7%, 8%, and 9%. In a further embodiment, the xylitol, fructose, sorbitol or other sweetener is added at between 4 and 8%. In a further embodiment, the sweetener is added at between 5 and 8%. Although it is to be understood that the strength of sweeteners known to one of skill in the art varies considerably and a much lower concentration may be needed, depending on the sweetener used.

Other substances may be added to the blend, including polyvinyl acetate and glycerol monostearate. The polyvinyl acetate may be added at a concentration of from 1 to 10% by weight, including 2%, 3%, 4%, 5%, 6%, 7%, 8%, and 9%. In a further embodiment, the polyvinyl acetate is added at a concentration of from 1 to 4% by weight, preferably from 2.5% to 3.5% by weight. The glycerol monostearate may be added at a concentration of from 0.1 to 10%, including 1%, 2%, 3%, 4%, 5%, 6%, 7%, 8%, and 9%. More preferably, the glycerol monstearate may be added at a concentration of from 0.3% to 3.3%, including 0.4%, 0.5%, 0.6%, 0.7%, 0.8%, 0.9%, 1.5%, 2.5%, and 3.25%.

The teeth whitening chewing gum formulations of the preferred embodiments preferably have one or more of the following advantages over the prior art: significantly decreased sensitivity to storage conditions due to greater stability at elevated temperatures, resulting in longer shelf life without requiring refrigeration; faster teeth whitening action resulting from accelerated generation of radical oxygen in contact with saliva; lower irritation potential to soft oral tissue due to absence or low concentrations of desiccating components in the formulation; tolerance of the presence of teeth mineralizing components such as calcium compounds and fluoride salts, which broadens the scope of benefits realized from the use of the devices of chewing gum described herein; tolerance of the presence of additives including sweeteners, flavors, fragrances and colorants and stability of such additives; such materials had a tendency to deteriorate in the presence of hydrogen peroxide present in prior art formulations; and simple and economical manufacturing procedure because the preferred embodiments allow for compounding of the device as a single component material.

Some unexpected advantages of the teeth whitening devices disclosed herein may be attributable to one or more of the following factors: thermal stability of peroxides of bivalent metals, particularly calcium, strontium and zinc peroxide; stability of such peroxides when stored in contact with anhydrous organic acids in an anhydrous environment; tolerance of said anhydrous mixtures of peroxides and acids to presence of alkaline substances, which have been proved beneficial for accelerating the rate of generation of radical oxygen; and ability of the mixtures of ingredients as described above to rapidly generate radical oxygen upon contact with saliva. It was also entirely unexpected that such mixtures of chemical components are acceptable, and can be made pleasing, from a sensory point of view (i.e., taste, smell, consistency, appearance, etc.).

Incorporation of fluoridizing compounds to the preferred embodiments, particularly fluoride salts such as sodium fluoride, stannous fluoride, or sodium monofluorophosphate, may provide additional oral health benefits, as will the presence of calcium ions resulting from the hydrolysis of reaction products of metal peroxides with organic acids.

The primary component of preferred devices is a gum base which is commonly employed in chewing gums known in the art. The chewing gum compositions may further comprise flavorings or other additives such as colorings.

The preferred embodiments are further illustrated by the following examples given to facilitate comprehension of the new technology without limiting its scope. All percentages given are by weight.

The compositions were made by blending the ingredients. The chewing gum base was normally introduced first, followed by introducing other ingredients. No special order of introduction is necessary. The following chewing gum formulations were produced using the above method.

EXAMPLE 1
The chewing gum teeth bleaching system consisted of:

| | |
|---|---|
| chewing gum base | 83% |
| calcium peroxide | 3.9% |
| calcium carbonate | 1.2% |
| citric acid | 8.9% |
| polyvinyl acetate | 3% |

EXAMPLE 2
The chewing gum teeth bleaching system consisted of:

| | |
|---|---|
| chewing gum base | 82.7% |
| calcium peroxide | 4.52% |
| calcium carbonate | 1.57% |
| citric acid | 8.0% |
| glycerol monostearate | 3.0% |
| peppermint oil | 0.2% |

EXAMPLE 3
The chewing gum teeth bleaching system consisted of:

| | |
|---|---|
| chewing gum base | 74.85% |
| calcium peroxide | 3.45% |
| calcium carbonate | 1.1% |
| citric acid | 10.43% |
| polyvinyl acetate | 2.9% |
| xylitol | 7.27% |

EXAMPLE 4
The chewing gum teeth bleaching system consisted of:

| | |
|---|---|
| chewing gum base | 73.1% |
| calcium peroxide | 3.4% |
| calcium carbonate | 1.1% |
| citric acid | 10.2% |
| zinc peroxide | 0.32% |
| polyvinyl acetate | 2.80% |
| saccharose | 8.9% |
| bubble gum flavoring | 0.18% |

EXAMPLE 5
The chewing gum teeth bleaching system consisted of:

| | |
|---|---|
| chewing gum base | 70.75% |
| calcium peroxide | 3.87% |
| calcium carbonate | 1.28% |
| citric acid | 9.9% |
| zinc peroxide | 0.7% |
| polyvinyl acetate | 2.75% |
| glycerol monostearate | 0.43% |
| sorbitol | 5.16% |
| fructose | 5.16% |

EXAMPLE 6
The chewing gum teeth bleaching system consisted of:

| | |
|---|---|
| chewing gum base | 70.2% |
| calcium peroxide | 6.32% |
| calcium carbonate | 2.22% |
| tartaric acid | 1.02% |
| citric acid | 8.54% |
| polyvinyl acetate | 2.56% |
| glycerol monostearate | 0.43% |
| peppermint oil | 0.17% |
| saccharose | 8.52% |
| sodium fluoride | 0.02% |

EXAMPLE 7
The chewing gum teeth bleaching system consisted of:

| | |
|---|---|
| chewing gum base | 70.48% |
| calcium peroxide | 3.35% |
| calcium carbonate | 1.06% |
| tartaric acid | 9.08% |
| polyvinyl acetate | 2.64% |
| glycerol monostearate | 0.44% |
| xylitol | 5.3% |
| saccharose | 5.3% |
| strawberry flavor | 0.35% |
| glycerine | 2.0% |

All chewing gum formulations of Examples 1–7 have exhibited satisfactory stability at ambient temperatures and the ability to generate radical oxygen in the oral environment.

What is claimed is:

1. A tooth whitening chewing gum, comprising:
one or more peroxides of the first or second group of the Periodic Table at concentrations corresponding to 1% to 20% by weight hydrogen peroxide and one or more anhydrous organic acids in a gum base; wherein said chewing gum is capable of whitening teeth when chewed.

2. The tooth whitening chewing gum of claim 1, wherein the one or more organic acids are at concentrations of from about 1% to about 20% by weight.

3. The tooth whitening chewing gum of claim 2, wherein the one or more organic acids are at concentrations of from about 8% to about 12% by weight.

4. The tooth whitening chewing gum of claim 1, wherein the one or more peroxides is at a concentration of about 3% to about 12% by weight hydrogen peroxide.

5. The tooth whitening chewing gum of claim 1, wherein the one or more organic acids are selected from the group consisting of tartaric acid, citric acid, lactic acid, and oxalic acid.

6. The tooth whitening chewing gum of claim 1, wherein the one or more peroxides are selected from the group consisting of calcium peroxide, zinc peroxide, and strontium peroxide.

7. The tooth whitening chewing gum of claim 1, wherein a water extract of the gum has a pH of about 4 to about 11.

8. The tooth whitening chewing gum of claim 1, further comprising a hydrophilic additive.

9. The tooth whitening chewing gum of claim 8, wherein said hydrophilic additive is selected from the group consisting of: glycerin, propylene glycol, and polyglycols.

10. The tooth whitening chewing gum of claim 1, further comprising a sweetener.

11. The tooth whitening chewing gum of claim 10, wherein said sweetener is selected from the group consisting of xylitol, fructose, sorbitol, sucrose, saccharine, and aspartame.

12. The tooth whitening chewing gum of claim 1, further comprising one or more additives selected from the group consisting of: food grade colorants, flavors, fragrances, and mixtures thereof.

13. The tooth whitening chewing gum of claim 12, wherein said colorant is FD&C Blue #1 or FD&C Blue #2.

14. The tooth whitening chewing gum of claim 12, wherein said flavor is selected from the group consisting of: orange, lemon, peppermint, spearmint, mint, bubble gum, cherry, watermelon, strawberry and apple varieties.

15. The tooth whitening chewing gum of claim 1, further comprising a fluoride salt.

16. The tooth whitening chewing gum of claim 15, wherein said fluoride salt is selected from the group consisting of: sodium fluoride, stannous fluoride, sodium monofluorophosphate, and mixtures thereof.

17. A tooth whitening chewing gum, comprising:
one or more peroxides of the first or second group of the Periodic Table at concentrations corresponding to 3% to 7% by weight hydrogen peroxide and one or more anhydrous organic acids selected from the group consisting of tartaric acid, citric acid, lactic acid, and oxalic acid at concentrations corresponding to 2 to 10% by weight in a gum base; wherein said chewing gum is capable of whitening teeth when chewed.

18. The tooth whitening chewing gum of claim 17 wherein said one or more organic acids are selected from the group consisting of citric acid, lactic acid, and oxalic acid.

19. The tooth whitening chewing gum of claim 17 wherein said one or more peroxides are selected from the group consisting of calcium peroxide, zinc peroxide, and strontium peroxide.

20. The tooth whitening chewing gum of claim 17, further comprising a hydrophilic additive.

21. The tooth whitening chewing gum of claim 17, further comprising a sweetener.

22. The tooth whitening chewing gum of claim 21, wherein said sweetener is selected from the group consisting of xylitol, fructose, sorbitol, sucrose, saccharine, and aspartame.

23. The tooth whitening chewing gum of claim 17, further comprising one or more additives selected from the group consisting of: food grade colorants, flavors, fragrances, and mixtures thereof.

24. The tooth whitening chewing gum of claim 17, further comprising a fluoride salt.

25. A tooth whitening chewing gum, said chewing gum comprising:
3% to 7% by weight of calcium peroxide, 0.5–6% by weight of calcium carbonate, and a total of about 1 to about 20% by weight of one or more anhydrous organic acids;
wherein the calcium peroxide, calcium carbonate and one or more acids are incorporated into a gum base to form a chewing gum.

26. The tooth whitening chewing gum of claim 25, wherein the one or more organic acids are at concentrations of from about 8% to about 12% by weight.

27. The tooth whitening chewing gum of claim 25, wherein the one or more peroxides is at a concentration of about 3% to about 7% by weight hydrogen peroxide.

28. The tooth whitening chewing gum of claim 25, wherein the one or more organic acids are selected from the group consisting of tartaric acid, citric acid, lactic acid, and oxalic acid.

29. The tooth whitening chewing gum of claim 25, wherein a water extract of the gum has a pH of about 4 to about 11.

30. The tooth whitening chewing gum of claim 25, further comprising a hydrophilic additive.

31. The tooth whitening chewing gum of claim 25, further comprising a sweetener.

32. The tooth whitening chewing gum of claim 31, wherein said sweetener is selected from the group consisting of xylitol, fructose, sorbitol, sucrose, saccharine, and aspartame.

33. The tooth whitening chewing gum of claim 25, further comprising one or more additives selected from the group consisting of: food grade colorants, flavors, fragrances, and mixtures thereof.

34. The tooth whitening chewing gum of claim 25, further comprising a fluoride salt.

35. A tooth whitening chewing gum, comprising:
one or more metal peroxides at concentrations corresponding to 3% to 12% by weight hydrogen peroxide;
0.5–6% by weight of one or more compounds selected from the group consisting of alkaline earth metal hydroxides, alkaline earth metal oxides, alkaline earth metal carbonates, sodium hydroxide, sodium carbonate, potassium hydroxide, potassium carbonate, and calcium silicate; and
one or more anhydrous organic acids in a gum base to form a chewing gum.

36. The tooth whitening chewing gum of claim 35, wherein the one or more organic acids are at concentrations of from about 1% to about 20% by weight.

37. The tooth whitening chewing gum of claim 35, wherein the one or more organic acids are at concentrations of from about 8% to about 12% by weight.

38. The tooth whitening chewing gum of claim 35, wherein the one or more peroxides is at a concentration of about 3% to about 7% by weight hydrogen peroxide.

39. The tooth whitening chewing gum of claim 35, wherein the one or more organic acids are selected from the group consisting of tartaric acid, citric acid, lactic acid, and oxalic acid.

40. The tooth whitening chewing gum of claim 35, wherein the one or more peroxides are selected from the group consisting of calcium peroxide, zinc peroxide, and strontium peroxide.

41. The tooth whitening chewing gum of claim 35, wherein a water extract of the gum has a pH of about 4 to about 11.

42. The tooth whitening chewing gum of claim 35, further comprising a hydrophilic additive.

43. The tooth whitening chewing gum of claim 35, further comprising a sweetener.

44. The tooth whitening chewing gum of claim 43, wherein said sweetener is selected from the group consisting of xylitol, fructose, sorbitol, sucrose, saccharine, and aspartame.

45. The tooth whitening chewing gum of claim 35, further comprising one or more additives selected from the group consisting of: food grade colorants, flavors, fragrances, and mixtures thereof.

46. The tooth whitening chewing gum of claim 35, further comprising a fluoride salt.

* * * * *